United States Patent [19]

Witte et al.

[11] Patent Number: 4,948,809
[45] Date of Patent: Aug. 14, 1990

[54] SULPHONYLALKYLAMINES, PROCESSES FOR THE PREPARATION THEREOF AND PHARMACEUTICAL COMPOSITIONS CONTAINING THEM

[75] Inventors: Ernst-Christian Witte, Mannheim; Hans-Peter Wolff, Hirschberg-Grossachsen; Karlheinz Stegmeier, Heppenheim; Johannes Pill, Leimen, all of Fed. Rep. of Germany

[73] Assignee: Boehringer Mannheim GmbH, Mannheim, Fed. Rep. of Germany

[21] Appl. No.: 281,955

[22] Filed: Dec. 5, 1988

Related U.S. Application Data

[63] Continuation of Ser. No. 913,717, Sep. 30, 1986, abandoned.

[30] Foreign Application Priority Data

Oct. 2, 1985 [DE] Fed. Rep. of Germany ....... 3535167

[51] Int. Cl.$^5$ ................. A61K 31/215; C07C 64/76
[52] U.S. Cl. ................. 514/538; 560/12; 560/10; 562/430; 564/86; 564/87; 564/88; 564/89; 564/92; 514/602; 514/603; 514/605; 514/562; 552/8
[58] Field of Search ............ 560/10, 12; 562/430; 564/86, 87, 88, 89, 92; 514/602, 603, 605, 562, 822, 538; 552/8

[56] References Cited

U.S. PATENT DOCUMENTS

| | | | |
|---|---|---|---|
| 4,219,668 | 8/1980 | Chiccarelli | 514/822 |
| 4,258,058 | 3/1981 | Witte et al. | 560/10 |
| 4,443,477 | 4/1984 | Witte et al. | 560/10 |
| 4,657,929 | 4/1987 | Ince et al. | 514/676 |

FOREIGN PATENT DOCUMENTS

194548 9/1986 European Pat. Off. .

OTHER PUBLICATIONS

*Chemical Abstracts*, 106:46666 (1987).

*Primary Examiner*—Richard L. Raymon
*Assistant Examiner*—Mark W. Russell
*Attorney, Agent, or Firm*—Felfe & Lynch

[57] ABSTRACT

The present invention provides sulphonylphenylalkylamines of the general formula:

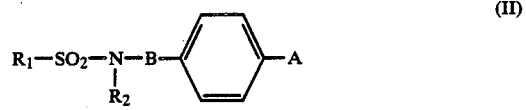

(II)

wherein $R_1$ is an alkyl radical containing up to 6 carbon atoms, a cycloalkyl radical containing 3–7 carbon atoms or an aralkyl, aralkenyl or aryl radical, the aryl moiety, in each case, being optionally substituted one or more times by halogen, $C_1$–$C_6$ alkyl, $C_1$–$C_6$ alkoxy, hydroxyl, trifluoromethyl, cyano, nitro, amino, $C_1$–$C_6$ alkylamino, $C_2$–$C_{12}$ dialkylamino, $C_1$–$C_6$ acylamino, $C_1$–$C_{16}$ acyl or azide, $R_2$ is a hydrogen atom, an alkyl radical containing up to 6 carbon atoms, an acyl radical or an aralkyl or aralkenyl radical, the aryl moiety, in each case, optionally being substituted one or more times by halogen, $C_1$–$C_6$ alkyl, $C_1$–$C_6$ alkoxy, hydroxyl, trifluoromethyl, cyano, nitro, amino, $C_1$–$C_6$ alkylamino, $C_1$–$C_{12}$ dialkylamino, $C_1$–$C_6$ acylamino, $C_1$–$C_{16}$ acyl or azide, B is an unbranched or branched alkylene chain with a maximum of 4 carbon atoms and A an alkyl or alkenyl radical containing up to 6 carbon atoms, a $C_1$–$C_6$ formylalkyl radical, a $C_1$–$C_6$ hydroxy-alkyl group or a radical —D—$R_3$, in which D is a

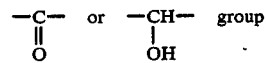

and $R_3$ is a hydrogen atom, a $C_1$–$C_5$ alkyl, a $C_1$–$C_5$ hydroxyalkyl or a $C_1$–$C_5$ alkylcarboxylic acid radical, as well as the pharmacologically acceptable salts thereof, the esters and amides thereof and the lactones of those compounds which contain a hydroxyl and a carboxyl group, with the exception of the compound benzene-sulphonic acid-(4-acetylphenethylamide).

The present invention also provides processes for the preparation of these compounds and pharmaceutical compositions containing them.

17 Claims, No Drawings

SULPHONYLALKYLAMINES, PROCESSES FOR THE PREPARATION THEREOF AND PHARMACEUTICAL COMPOSITIONS CONTAINING THEM

This application is a continuation, division, of application Ser. No. 913,717, filed Sept. 30, 1986, now abandoned.

The present invention is concerned with new sulphonylphenylalkylamines substituted on the phenyl moiety in the 4-position and with derivatives thereof, as well as with processes for the preparation thereof and pharmaceutical compositions which contain these compounds.

European Patent Specification No. 0031954 describes sulphonamides with a lipid-sinking and thrombocyte aggregation-inhibiting action which are compounds of the general formula:

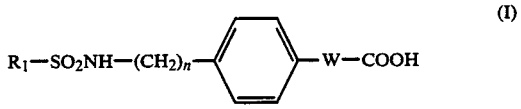

wherein $R_1$ is an aryl, aralkyl or aralkenyl radical, n is 2 or 3 and W is a valency bond or an unbranched or branched alkylene chain containing up to 4 carbon atoms, the latter being either saturated or containing a double bond(see also U.S. Pat. No. 4,443,477).

We have now, surprisingly, found that compounds with a lipid-sinking and thromboxane-$A_2$ antagonistic action are obtained when, in general formula (I), the —W—COOH radical is replaced by an alkyl radical containing up to 6 carbon atoms, which can be substituted by oxygen-containing functions.

Thus, the present invention provides new sulphonylphenylalkylamines of the general formula:

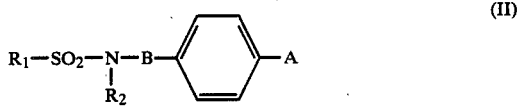

wherein $R_1$ is an alkyl radical containing up to 6 carbon atoms, a cycloalkyl radical containing 3–7 carbon atoms or an aralkyl, aralkenyl or aryl radical, the aryl moiety, in each case, being optionally substituted one or more times by halogen, $C_1$–$C_6$ alkyl, $C_1$–$C_6$ alkoxy, hydroxyl, trifluoromethyl, cyano, nitro, amino, $C_1$–$C_6$ alkylamino, $C_2$–$C_{12}$ dialkylamino, $C_1$–$C_6$ acylamino, $C_1$–$C_{16}$ acyl or azide, $R_2$ is a hydrogen atom, an alkyl radical containing up to 6 carbon atoms, an acyl radical or an aralkyl or aralkenyl radical, the aryl moiety, in each case, optionally being substituted one or more times by halogen, $C_1$–$C_6$ alkyl, $C_1$–$C_6$ alkoxy, hydroxyl, trifluoromethyl, cyano, nitro, amino, $C_1$–$C_6$ alkylamino, $C_2$–$C_{12}$ dialkylamino, $C_1$–$C_6$ acylamino, $C_1$–$C_{16}$ acyl or azide, B is an unbranched or branched alkylene chain with a maximum of 4 carbon atoms and A an alkyl or alkenyl radical containing up to 6 carbon atoms, a $C_1$–$C_6$ formylalkyl radical, a $C_1$–$C_6$ hydroxyalkyl group or a radical —D—$R_3$, in which D is a

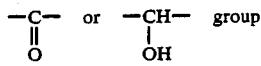

and $R_3$ is a hydrogen atom, a $C_1$–$C_5$, alkyl a $C_1$–$C_5$ hydroxyalkyl or a $C_1$–$C_5$ alkylcarboxylic acid radical, as well as the pharmacologically acceptable salts thereof, the esters and amides thereof and the lactones of those compounds which contain a carboxyl group or a hydroxyl and a carboxyl group, with the exception of the compound benzenesulphonic acid-(4-acetylphenethylamide).

Benzenesulphonic acid-(4-acetylphenethylamide) is described in European Patent Specification No. 0031954 as an intermediate for the preparation of the carboxylic acids described therein without any mention being made of a pharmacological action.

The new compounds of the general formula (II) display an excellent antagonistic action towards thromboxane $A_2$, as well as against prostaglandin endoperoxides. They inhibit the aggregation of blood platelets and prevent the constriction of the smooth musculature, as well as bronchoconstriction. Furthermore, they are valuable for the treatment of pathological changes of the kidney function.

These properties make them valuable for the treatment of, for example, cardiovascular diseases and of asthma and for the prophylaxis of a shock lung. Furthermore, they can be used in cases of organ transplantations and kidney dialysis and are useful for preventing relapse in cases of stomach ulcers. A special importance lies in the possibility favourably to influence thromboptic processes or to prevent them. They can be used for the treatment of peripheral arterial occlusive diseases and can be used,for example, against cerebral ischaemic states.

In addition, they are able to inhibit the incorporation of acetate into cholesterol and can, therefore, also be used for the treatment of fat metabolism diseases.

When $R_1$ is an alkyl radical, it is to be understood to be an unbranched or branched alkyl radical containing up to 6 carbon atoms, methyl, ethyl and hexyl radicals being preferred.

When $R_1$ is a cycloalkyl radical, it can be, for example, a cyclopropyl, cyclopentyl or cyclohexyl radical.

An aryl radical, alone or in combination with an alkyl or alkylene chain, is to be understood to be, in all cases, an aromatic hydrocarbon radical containing 6–14 carbon atoms and especially a phenyl, biphenylyl, naphthyl or fluorenyl radical. These aryl radicals can be substituted one or more times in all possible positions, the substituents being halogen, $C_1$–$C_6$ alkyl. $C_1$–$C_6$ alkoxy, hydroxyl, trifluoromethyl, cyano, nitro, amino, $C_1$–$C_6$ alkylamino, $C_2$–$C_{12}$dialkylamino, $C_1$–$C_6$ acylamino, $C_1$–$C_6$ acyl and azide. Preferred substituents include, for example, methoxy, ethoxy, methyl, ethyl, propyl, tert.-butyl, acetylamino, acetyl, methylamino, dimethylamino, ethylamino and diethylamino radicals.

As aralkyl radicals $R_1$, those come into question the straight-chained or branched alkylene part of which contains 1–5 carbon atoms. Preferred aralkyl radicals $R_1$ are the phenethyl and the 4-chlorophenethyl radical.

Aralkenyl radicals $R_1$ are to be understood to be those in which the alkenyl moiety contains 2 or 3 carbon atoms, the styryl and 4-chlorostyryl radicals being preferred.

Halogen is to be understood to be fluorine, chlorine or bromine.

The alkyl radicals $R_2$ are straight-chained and branched containing up to 6 carbon atoms, the methyl radical being preferred. An aralkyl radical $R_2$ is to be understood to be one in which the alkylene moiety contains up to 5 carbon atoms, preferred aralkyl radicals including benzyl, 4-chlorobenzyl, phenethyl and 4-chlorophenethyl radicals.

An aralkenyl radical $R_2$ is to be understood to be one in which the alkenylene moiety contains 3 or 4 carbon atoms, cinnamyl and 4-chlorocinnamyl radicals being preferred.

The acyl radicals are derived from aliphatic carboxylic acids containing 2-16 carbon atoms or from araliphatic or aromatic carboxylic acids, preferred acyl radicals including acetyl, isobutyroyl, cinnamoyl, benzoyl, 4-chlorobenzoyl, 4-aminobenzoyl, n-octanoyl and n-hexadecanoyl.

B is an alkylene chain containing up to 4 carbon atoms, the following alkylene chains being preferred:

$$-CH_2-, \ -(CH_2)_2-, \ -(CH_2)_3-, \ -\underset{\underset{CH_3}{|}}{CH}- \ \text{and} \ -CH_2-\underset{\underset{CH_3}{|}}{CH}-.$$

A can be an alkyl radical containing up to 6 carbon atoms which can be substituted by oxygen-containing functions, such as oxo or hydroxyl groups and possibly additional carboxyl groups.

The groups A set out in the following are preferred:
1. an unbranched or branched alkyl radical containing 2-6 carbon atoms which is saturated or unsaturated once, preferably ethyl, n-propyl, n-butyl or propenyl.
2. an unbranched or branched saturated alkyl radical which carries a terminal hydroxyl group and especially one of the general formula $$-(CH_2)_p-OH$$

in which p is a whole number of from 1 to 6.
3. an acyl radical $-CO-R_3$, wherein
   (a) $R_3$ is a hydrogen atom (formyl radical); or
   (b) $R_3$ is an unbranched or branched saturated alkyl radical containing up to 5 carbon atoms, methyl, ethyl, n-propyl and n-butyl being preferred; or
   (c) $R_3$ is an unbranched or branched saturated alkyl radical containing up to 5 carbon atoms which carries a terminal hydroxyl group, preferred radicals of this type being those of the general formula:

$$R_3 = -(CH_2)_{p-1}-OH$$
   in which p is 3, 4 or 5; or
   (d) $R_3$ is an unbranched or branched alkyl radical with a terminal carboxyl function, preferred radicals of this type being those of the general formula:

$$R_3 = -(CH_2)_{p-2}-COCH$$
   in which p is 2 to 6 and especially 4 to 6.
4. A is a $$-\underset{\underset{OH}{|}}{CH}-R_3 \text{ radical,}$$

$R_3$ having the above-given meaning.

When $R_3$ is an alkyl radical as defined under 3, it is preferably a methyl, ethyl, n-propyl or n-butyl radical.

If, on the other hand, $R_3$ is an alkyl radical with a terminal hydroxyl group, then it is preferably a radical of the general formula:

$$R_3 = -(CH_2)_{p-1}-OH,$$
wherein p is 3, 4 or 5.

If $R_3$ represents an alkyl radical with a terminal carboxyl function, then it is preferably a radical of the general formula:

$$R_3 = -(CH_2)_{p-2}-COOH$$
wherein p is 4 or 5.

Especially preferred are compounds of general formula (II), wherein $R_1$ is a methyl, ethyl or n-hexyl radical, a cyclohexyl radical, a phenethyl or styryl radical, in which the phenyl moiety can be substituted by halogen, a phenyl radical which is optionally substituted by halogen, methyl, isopropyl, trifluoromethyl, methoxy, hydroxyl, cyano, nitro, azido, acetyl or acetylamino, or a naphthyl radical or a biphenyl radical which can be substituted by halogen, $R_2$ is a hydrogen atom, a methyl, acetyl, octanoyl or hexadecanoyl radical, a benzoyl radical optionally substituted by halogen, or a benzyl, phenethyl or cinnamyl radical, the phenyl moiety of which can be substituted by halogen, B is a methylene, ethylene or propylene radical and A is an ethyl. propyl, butyl or pentyl radical which is optionally substituted once or twice by hydroxyl, carboxyl, formyl, acetoxy or benzoyloxy, or a hydroxymethyl, formyl, propenyl or acetylvinyl radical or an acetyl, propionyl or butyryl radical which, in each case, can be substituted by hydroxyl, carboxyl, ethoxycarbonyl or methoxycarbonyl, as well as the pharmacologically acceptable salts thereof, the esters and amides thereof and the lactones of those compounds which contain a hydroxyl and carboxyl group.

In all cases, the term "carboxyl function" is also to be understood to include esters and amides of such carboxylic acids.

The esters can be those formed from lower monohydroxy alcohols, for example, methanol or ethanol, or from polyhydroxy alcohols, for example glycerol, as well as from those alcohols which also contain other functional groups, for example ethanolamine.

The present invention also includes the "inner esters" of the hydroxycarboxylic acids of suitable chain length, i.e. the lactones.

When A contains at least one asymmetrical carbon atom, then the present invention also includes not only the pure optical isomers but also the mixtures/racemates thereof. If the radical A contains at least one double bond, then the present invention also includes the pure E and Z isomers, as well as mixtures thereof.

The present invention also includes a process for the preparation of the compounds of general formula (II), wherein
(a) an amine of the general formula:

(III)

HN—B—⟨phenyl⟩—A,
|
$R_2$ in which $R_2$, B and A have the above-given meanings, or a salt thereof, is reacted in per se known manner with a sulphonic acid of the general formula $$R_1-SO_2OH \quad \quad (IV),$$

in which $R_1$ has the above-given meaning, or with a derivative thereof; or (b) a sulphonamide of the general formula:

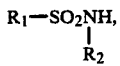  (V)

in which $R_1$ and $R_2$ have the same meanings as above, is reacted with a compound of the general formula:

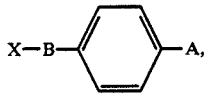  (VI)

in which X is a reactive group and A has the same meaning as above.

If A is to contain at least one hydroxyl group, in some cases it is advantageous to use a compound (VI) which, instead of the hydroxyl group, contains an oxo group or an ester function (or possibly both). Subsequent to the reaction having taken place between (V) and (VI), these groups are reduced to hydroxyl functions. (c) For the preparation of compounds (II), in which $R_2$ has the above-given meaning other than a hydrogen atom, they can also be obtained by the subsequent introduction of $R_2$ by reacting a compound of the general formula:

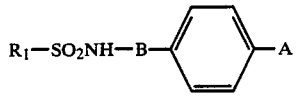  (IIa)

in which A, B and $R_1$ have the same meanings as above, with a compound of the general formula:

$R_2-X$  (VII)

in which X is as defined above and $R_2$ has the above meaning other than a hydrogen atom.

In the case of the presence of hydroxyl groups in the radical A, that said under (b) applies accordingly. (d) For the introduction of hydroxyl groups into the radical A, the following processes can be used:
1. reduction of a carbonyl group
2. reduction of a carboxylic acid or of a carboxylic acid ester function
3. simultaneous reduction of both.

(e) The introduction of double bonds into the radical A can take place in that, from a radical A containing the group:

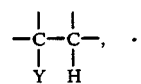  (VIII)

in which Y is a halogen atom or a hydroxyl group or a functionally changed hydroxyl group, HY is split off, ($e_2$) A further possibility is the reaction of oxo compounds with appropriate organophosphorus compounds in the manner of a modified Wittig reaction. In this case, as starting materials there are used compounds of the general formula (II), in which ($\alpha$) A = 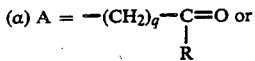 or ($\beta$) A = 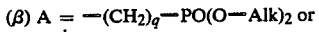 or ($\gamma$) A = 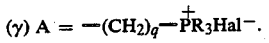.

(f) By the hydrogenation of compounds with an unsaturated radical A obtained according to (e), there are obtained corresponding compounds with a saturated hydrocarbon chain. Such compounds can also be prepared by the reduction of keto groups contained in A.

As reactive derivatives of the sulphonic acids (IV), it is especially preferred to use halides, as well as esters. The reactions of the sulphonic acid halides with compounds of the general formula (III) preferably takes place with the addition of an acid-binding agent, for example an alkali metal acetate, sodium hydrogen carbonate, sodium carbonate, sodium phosphate, calcium oxide, calcium carbonate or magnesium carbonate. However, this function can also be taken over by an organic base, for example pyridine or triethylamine. As inert solvent, there can be used, for example, diethyl ether, benzene, methylene chloride, dioxan or an excess of tertiary amine.

When using an inorganic acid binder, as reaction medium there can also be used, for example, water, aqueous ethanol or aqueous dioxan.

For the alkylation of sulphonamides (V), there can be used compounds (VI), in which X is a halogen atom, such as a chlorine or bromine atom but preferably those in which X is an arylsulphonyloxy radical. Thus, the alkylation agent is preferably an arylsulphonic acid alkyl ester, a method which is described, in its application to sulphonic acid amides, for example by Klammann et al. (Monatshefte fuer Chemie, 83, 871/1952). The reaction takes place in an alkaline medium, a hot concentrated solution of sodium carbonate being preferred as the reaction medium. If, on the other hand, X is a halogen atom, then an alkali metal salt of the sulphonamide (V), for example the sodium salt, is reacted with (VI) (X=chlorine or bromine) in polar solvent, for example dimethylformamide. In order to avoid a disubstitution of the sulphonamide (V), it is preferred to use (V) in excess.

If, subsequent to the sulphonamide formation, a group $R_2$ is to be introduced, then this can take place by reaction of a compound (II), in which $R_2$ is a hydrogen atom, with an acid halide, when $R_2$ is to be an acyl radical For all other meanings of $R_2$, there is used a halide (chloride or bromide) of general formula (VII), working under the above-described conditions.

The acylation of the sulphonamide takes place in an inert solvent, such as diethyl ether or methylene chloride. The acid-binding agent used is preferably an organic base, such as pyridine or triethylamine.

Conversions in the radical A possibly carried out after the sulphonamide formation and possibly after introduction of a group $R_2$, can be described as follows:

For the conversion of a carbonyl group into a hydroxyl group, all conventional processes can here be used. It is preferred to use a reduction with a complex borohydride, for example with sodium borohydride, a protic solvent, such as water, an aqueous alcohol or aqueous dioxan serving as the reaction medium. In the case of the absence of other reducible groups, the reduction can also be carried out with a complex aluminium hydride, such as lithium aluminium hydride, in which case an aprotic solvent, such as diethyl ether, tetrahydrofuran or dioxan, is used as the reaction medium. However, the carbonyl reduction can also take place with catalytically activated hydrogen, for example with hydrogen/Raney nickel, or by reaction with nickelaluminium alloy in aqueous alkali.

For the reduction of the carboxyl function, all conventional reducing agents can be used, for example complex hydrides, such as lithium aluminium hydride, or borane adducts, such as $BH_3$. THF. However, the reduction can also take place advantageously by the reduction of a derivative of the carboxylic acid, for example of a mixed anhydride of the carboxylic acid and a carbonic acid hemiester. As reducing agent, it is here preferable to use a complex borohydride, for example sodium borohydride, in a protic solvent.

Derivatives of the carboxylic acids which can h=used for the reduction are, for example, also their esters which can be reacted to give primary alcohols according to methods known from the literature. Here, too, preferred reducing agents are complex aluminium hydrides, for example lithium aluminium hydride.

If the carboxyl function is to be reduced without an oxo group simultaneously present in A also being reduced, then the latter is to be temporarily protected, for example by ketalisation. Such hydroxy-ketones can also be prepared by reducing not only the keto group but also the carboxyl function (whereby diols according to the present invention are obtained) and subsequently selectively oxidising the secondary hydroxyl function to the keto function. For this purpose, there can be used, for example, active manganese dioxide.

For the introduction of double bonds into the radical A, there can be used all conventional elimination reactions:

Splitting off water from hydroxy compounds (acid catalysed, by heating with, for example sulphuric acid or 95% phosphoric acid); splitting off a hydrogen halide from a halide and of a sulphonic acid from a sulphonyloxy compound (for example a tosyloxy compound) by means of a strong base, such as potassium tert.-butanolate or DBU, or splitting off acetic acid from an acetoxy compound or xanthogenic acid from a xanthogenate by heating.

For the formation of groups A which contain a double bond, there can also be used the condensation of two components, one of which contains an oxo group and the other of which contains a phosphonium salt group (Wittig reaction) or a phosphonate group (Wittig-Horner-Emmons reaction). These reactions can be carried out in a large variety of solvents, for example water, methanol, dimethylformamide, ethylene glycol or glycol ethers, and proceed in the presence of a base, for example sodium carbonate, a sodium alcoholate, sodium hydride or butyl lithium, whereby, depending upon the reaction conditions, there can result cis or trans isomers or mixtures of both.

The preparation of compounds in which A is a saturated alkyl chain ca be accomplished by the hydrogenation of an olefinic A. The hydrogenation is preferably carried out at normal pressure or under increased pressure in the presence of a metal catalyst, for example palladium or platinum, in a solvent, for example acetic acid or a lower alcohol.

Also preferred is the reduction of compounds which contain a hydroxyl or an oxo group in the radical A. The reduction of hydroxyl group-containing compounds takes place in the presence of a strong acid, for example a trace of perchloric acid, by means of hydrogen with the help of palladium or platinum catalyst. Numerous processes can be used for the reduction of an oxo group. The reduction can take place, for example, according to Clemmensen by means of zinc/hydrochloric acid or by first forming a tosyl hydrazone from the ketone followed by reduction. However, here, too, it is preferred to carry out the reduction by mean of catalytically activated hydrogen under the above-described conditions.

For the preparation of salts with pharmacologically acceptable organic or inorganic bases, for example sodium hydroxide, potassium hydroxide, calcium hydroxide, ammonium hydroxide, methylglucamine, morpholine or ethanolamine, the carboxylic acids can be reacted with the corresponding bases. Mixtures of carboxylic acids with an appropriate alkali metal carbonate or hydrogen carbonate can also be considered.

For the preparation of pharmaceutical compositions, compounds of general formula (II) are mixed in known manner with appropriate pharmaceutical carrier substances, aroma, flavouring and colouring materials and formed, for example, into tablets or dragees or, with the addition of appropriate adjuvant materials, suspended or dissolved in water or an oil, for example olive oil.

The compounds of general formula (II) can be administered orally or parenterally in liquid or solid form. As injection medium, water is preferably used which contains the stabilising agents, solubilising agents and/or buffers usual in the case of injection solutions. Such additives include, for example, tartrate and borate buffers, ethanol, dimethylsulphoxide, complex formers (such as ethylenediamine-tetraacetic acid), high molecular weight polymers (such as liquid polyethylene oxide) for viscosity regulation and polyethylene derivatives of sorbit anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage administered depends upon the age, the state of health and weight of the recipient, the extent of the disease, the nature of further treatments possibly carried out simultaneously, the frequency of the treatments and the nature of the desired action. Usually, the daily dosage of the active compound is from 0.1 to 50 mg./kg. of body weight. Normally, 0.5 to 40 and preferably 1.0 to 20 mg./kg./day in one or more administrations per day are effective in order to obtain the desired results.

The following Examples are given for the purpose of illustrating the present invention:

EXAMPLE 1.

4-Chlorobenzenesulphonic acid-(4-acetylohenethylamide)

A suspension of 10.0 g. (50 mmole) 4-acetylphenethylamide hydrochloride 80 ml. methylene chloride and 12.7 g. (125 mmole) triethylamine is stirred for about 30 minutes and then a solution of 11.8 g. (56 mmole) 4-chlorobenzenesulphonyl chloride in 50 ml. methylene chloride is slowly added dropwise thereto at 0°C. After stirring at ambient temperature for 2 hours, the reaction mixture is diluted with methylene chloride, washed with water, dilute hydrochloric acid and again with water, then dried with anhydrous sodium sulphate and evaporated. The crude product obtained is recrystallised twice from ethanol. Yield 11.7 g. (69% of theory); m.p. 97°–99° C.

Analogously thereto, by the reaction of various sulphonic acid chlorides with the appropriate amine components, there are prepared the following compounds:

(2) ethyl 4-{4-2-(benzenesulphonylamino)-ethyl-phenyl}-4-butanoate; yield 91% of theory; m.p. 77° C. (recrystallised from toluene+heptane)

(3) 4-chlorobenzenesulphonic acid-(4-acetylbenzylamide); yield 41% of theory; m.p. 132°–133° C. (recrystallised from toluene)

(4) benzenesulphonic acid-(4-acetylphenethylamide); the reaction here takes place in pure pyridine: yield 42% of theory; m.p. 140°–141° C. (recrystallised from (5) 3,4-dichlorobenzenesulphonic acid-(4-acetylphenethylamide); yield 80% of theory; m.p. 132°–133° C. (recrystallised from toluene)

(6) 4-bromobenzenesulphonic acid-(4-acetylphenethylamide): yield 91% of theory: m.p. 130°–131° C. (recrystallised from toluene)

(7) 4-fluorobenzenesulphonic acid-(4-acetylphenethylamide): yield 72% of theory; m.p. 106°–107° C. (recrystallised from ethyl acetate)

(8) 4-methoxybenzenesulphonic acid-(4-acetylphenethylamide): yield 86% of theory; m.p. 122°–123° C. (recrystallised from isopropanol)

(9) 4-isopropylbenzenesulphonic acid-(4-acetylphenethylamide); yield 66% of theory; m.p. 124°–126° C. (recrystallised from ethanol)

(10) methanesulphonic acid-(4-acetylphenethylamide): yield 40% of theory; m.p. 80°–81° C. (recrystallised from toluene)

(11) 3-chlorobenzenesulphonic acid-(4-propionylphenethylamide); yield 96% of theory; m.p. 136°–139° C. (recrystallised from toluene)

(12) ethyl 4-{4-2-(4-chlorobenzenesulphonylamino)-ethyl-phenyl}-4-oxobutanoate; yield 90% of theory; m.p. 108°–109° C. (recrystallised from ethanol)

(13) 4-chlorobenzenesulphonic acid-(4-propionylbenzylamide); yield 89% of theory; m.p. 128° C. (recrystallised from toluene)

(14) benzenesulphonic acid-(4-propionylphenethylamide): yield 77% of theory; m.p. 116° C. (recrystallised from ethanol); oxime: m.p. 119°–120° C.

(15) 2-chlorobenzenesulphonic acid-(4-propionylphenethylamide); yield 84% of theory; m.p. 102°–103° C. (recrystallised from isopropanol)

(16) 4-chlorobenzenesulphonic acid-(4-propionylphenethylamide); yield 82% of theory; m.p. 101°–102° C. (recrystallised from heptane+toluene)

(17) 4-bromobenzenesulphonic acid-(4-propionylphenethylamide); yield 88% of theory; m.p. 99° C. (recrystallised from ethanol)

(18) 4-methoxybenzenesulphonic acid-(4-propionylphenethylamide) yield 82% of theory; m.p. 107° C. (recrystallised from isopropanol)

(19) 4-hydroxybenzenesulphonic acid-(4-propionylphenethylamide); yield 45% of theory; m.p. 125°–126° C. (recrystallised from isopropanol)

(20) 4-cyanobenzenesulphonic acid-(4-propionylphenethylamide); yield 75% of theory m.p. 126°–127° C. (recrystallised from isopropanol)

(21) benzenesulphonic acid-(4-butyroylphenethylamide); yield 67% of theory; m.p. 88°–90° C. (recrystallised from isopropanol)

(22) 4-chlorobenzenesulphonic acid-(4-butyroylphenethylamide); yield 82% of theory; m.p. 87°–88° C. (recrystallised from toluene+heptane)

(23) 4-acetylaminobenzenesulphonic acid-(4-butyroylphenethylamide); yield 78% of theory; m.p. 141°–143° C. (recrystallised from methanol)

(24) 4-chlorobenzenesulphonic acid-3-(4-butyroylphenyl)-propylamide.; yield 85% of theory; m.p. 77°–78° C. (recrystallised from toluene)

(25) ethyl 4-{4-2-4-(4-chlorophenyl)-benzenesulphonylamino-ethyl-phenyl}-b 4-oxobutanoate; yield 89% of theory: m.p. 157°–158° C. (recrystallised from toluene)

(26) ethyl - 4-{4-2-(2-naphthalene-1-sulphonylamino)-ethyl-phenyl}-4-oxobutanoate; yield 71%, of theory; colourless oil

(27) ethyl 5-{4-2-(4-chlorobenzenesulphonylamino)-ethyl-phenyl}-5-oxopentanoate; yield 97% of theory; m.p. 98°–99° C. (recrystallised from ethyl acetate)

The 4-propionylphenethylamine used as starting material is prepared in the following way:

To a suspension of 142.5 g. (1.55 mole) propionyl chloride, 96.5 g. (0.6 mole) N-acetylphenethylamine and 450 ml. 1,1,2,2-tetrachloroethane is added portionwise, with stirring at 0°–5° C., 260 g. (1.95 mole) aluminium chloride. Stirring is continued for 5 hours with ice cooling and finally the reaction mixture is poured on to ice. The organic phase is separated off, the aqueous phase is extracted with methylene chloride, the methylene chloride solution is combined with the tetrachloroethane solution and washed twice with water. After drying with anhydrous sodium sulphate, the solution is evaporated in a vacuum and the residue is recrystallised from an ethyl acetate-ligroin mixture. Yield 96.1 g. (73% of theory) 4-propionyl-N-acetylphenethylamine; m.p. 94.5°–95° C.

A mixture of 60.0 g. (273 mmole) 4-propionyl-N-acetylphenethylamine and 500 ml. 4H hydrochloric acid is heated for 10 hours in a boiling waterbath, then evaporated in a vacuum and the residue is recrystallised from ethanol. Yield 47.8 g. (82% of theory) 4propionyl-phenethylamine hydrochloride; m.p. 223°–224° C.

The 4-butyroylphenethylamine used as starting material is prepared in an analogous way:
4-butyroyl-N-acetylphenethylamine; yield 87% of theory; m.p. 99°–101° C. (recrystallised from water)
4-butyroylphenethylamine: yield 89% of theory; m.p. of the hydrochloride: 228°–231° C.

EXAMPLE 2.

4-Bromobenzenesulphonic acid-4--(1-hydroxyethyl)-phenethylamide.

11.4 g. (29.8 mmole) 4-Bromobenzenesulphonic acid(4-acetylphenethylamide) are dissolved in a mixture of 40 ml. methanol and 100 ml. ethanol and 0.85 g. (22.4 mmole) sodium borohydride then added portionwise thereto at 0° C. Subsequently, the reaction mixture is stirred at ambient temperature for 2 hours and then evaporated in a vacuum. After the addition of dilute hydrochloric acid, the reaction mixture is shaken out with methylene chloride and the methylene chloride phase is dried with anhydrous sodium sulphate Thereafter, it is evaporated and the residue is recrystallised from toluene. Yield 10.4 g. (91% of theory): m.p. 125°–127° C.

The following compounds are prepared analogously:
(2) ethyl 5-{4-2-(4-chlorobenzenesulph-onylamino)-ethyl-phenyl}-5-hydroxypentanoate; yield 74% of theory; m.p. 89°–90° C. (recrystallised from toluene+ligroin); from ethyl 5-{4-2-(4-chlorobenzenesulphonylamino)-ethyl-phenyl}-5-oxopentanoate
(3) 4-chlorobenzenesulphonic acid-4-(1-hydroxyethyl)-benzylamide; yield 85% of theory; m.p. 103°–104° C. (recrystallised from toluene)
(4) benzenesulphonic acid-4-(1-hydroxyethyl)-phenethylamide: yield 64% of theory; m.p. 98°–100° C. (recrystallised from toluene)
(5) 4-chlorobenzenesulphonic acid-4-(1-hydroxyethyl)-phenethylamide; yield 82% of theory: m.p. 105°–107° C. (recrystallised from toluene)
(6) 3,4-dichlorobenzenesulphonic acid-4-(1-hydroxyethyl)-phenethylamide; phenethylamide.; yield 96% of theory; m.p. 108°–109° C. (recrystallised from heptane+toluene)
(7) 4-fluorobenzenesulphonic acid-4-(1-hydroxyethyl)-phenethylamide; yield 73% of theory: m.p. 99° C. (recrystallised from ethyl acetate)
(8) 4-methoxybenzenesulphonic acid-4-(1-hydroxyethyl)-phenethylamide; yield 73% of theory; m.p. 84°–85° C. (recrystallised from toluene) and from the appropriate benzenesulphonic acid-(4-propionyl-phenethylamides), the following compounds:
(9) 4-chlorobenzenesulphonic acid-[4-(1-hydroxypropyl)-benzylamide]; yield 48% of theory; m.p. 102°–103° C. (recrystallised from toluene)
(10) benzenesulphonic acid-[4-(1-hydroxypropyl)-phenethylamide]; yield 62% of theory; m.p. 107° C. (recrystallised from ethyl acetate)
(11) 3-chlorobenzenesulphonic acid-[4-(1-hydroxypropyl)-phenethylamide]; yield 95% of theory; honey-like
(12) 4-chlorobenzenesulphonic acid-[4-(1-hydroxypropyl)-phenethylamide]; yield 62% of theory; m.p. 135°–136° C. (recrystallised from toluene)
(13) 4-bromobenzenesulphonic acid-[4-(1-hydroxypropyl)-phenethylamide]; yield 96% of theory; m.p. 148°–149° C. (recrystallised from ethanol).

From the appropriate benzenesulphonic acid-(4-butyroylphenethylamides), the following compounds are prepared analogously:
(14) benzenesulphonic acid-[4-(1-hydroxybutyl)-phenethylamide]; yield 73% of theory; m.p. 107°–108° C. (recrystallised from aqueous ethanol)
(15) 4-chlorobenzenesulphonic acid-[4-(1-hydroxybutyl)-phenethylamide]; yield 90% of theory; m.p. 127°–128° C. (recrystallised from toluene)
(16) 4-chlorobenzenesulphonic acid-{3-[4-(1-hydroxybutyl)-phenyl]-propylamide}; yield 95% of theory; m.p. 78°–79° C. (recrystallised from heptane+toluene).

EXAMPLE 3

Benzenesulphonic acid-(4-n-propylphenethylamide)

(a) 4-n-Propyl-N-acetylphenethylamide

A methanolic solution of 4-propionyl-N-acetylphenethylamine is hydrogenated in a shaking bomb at ambient temperature and normal pressure in the presence of palladium-on-charcoal catalyst and then filtered off with suction. The filtrate is evaporated in a vacuum to give quantitative yield of 4-n-propyl-N-acetylphenethylamine; m.p. 52° C.

(b) 4-n-Propylthenethylamine

A mixture of 9.3 g. (45 mmole) 4-n-propyl-N-acetylphenethylamine, 68 ml. 2N aqueous sodium hydroxide solution and 40 ml. ethanol is refluxed for 20 hours, cooled and acidified with hydrochloric acid. Thereafter, the ethanol is distilled off and the aqueous phase is extracted with ethyl acetate. It is rendered strongly alkaline with potassium hydroxide, extracted several times with diethyl ether and the combined ether phases are dried with potassium hydroxide and evaporated. There are obtained 4.6 g. (62% of theory) of an oily product which, without further purification, is used for the next reaction.

(c) Benzenesulphonic acid (4-n-propylphenethylamide).

The product obtained according to (b) is reacted analogously to Example 1 with benzenesulphochloride. Yield 66% of theory; colourless oil.

EXAMPLE 4

4-Chlorobenzenesulphonic acid-[4-(1-propenyl)-phenethylamide]

(a) 4-Chlorobenzenesulphonic acid-[4-(1-chloropropyl)-phenethylamide].

A mixture of 26.7 g. (75.4 mmole) 4-chlorobenzenesulphonic acid-4-(1-hydroxypropyl)-phenethyamide], 200 ml. methylene chloride and 100 ml. concentrated hydrochloric acid is vigorously stirred for 1 hour, then diluted with water and the methylene chloride phase is separated off. It is washed with water and sodium bicarbonate solution, dried with anhydrous sodium sulphate and evaporated. Yield quantitative; m.p. 90°–91° C.

(b) 4-Chlorobenzenesulphonic acid-[4-(1-propenyl)-phenethylamide]

1.86 g. (5 mmole) of the product obtained according to (a) are heated to 150° C. in a stream of nitrogen until the evolution of hydrogen chloride subsides. Thereafter, it is taken up in methylene chloride, stirred with silica gel, filtered with suction and the filtrate evaporated. The residue is dissolved in toluene and chromatographed on a short silica gel column. Yield: 1.04 g. (62% of theory); m.p. 149°–150° C.

The following compounds are prepared in an analogous way:
(2) (a) benzenesulphonic acid-[4-(1-chloropropyl)-phenethylamide]; yield 96% of theory; m.p. 56°–57° C. and therefrom
(b) benzenesulphonic acid-[4-(1-propenyl)-phenethylamide]; yield 65% of theory; m.p. 40°–43° C.
(3) (a) 4-bromobenzenesulphonic acid-[4-(1-chloropropyl)-phenethylamide]; yield 96% of theory; m.p. 83°–85° C. and therefrom
(b) 4-bromobenzenesulphonic acid-[4-(1-propenyl)-phenethylamide]; yield 34% of theory; m.p. 153°–155° C.

EXAMPLE 5

4-Chlorobenzenesulphonic acid-(4-formylphenethylamide)

A mixture of 11.0 g. (33.8 mmole) 4-chlorobenzenesulphonic acid-(4-hydroxymethylphenethylamide), 250 ml. methylene chloride and 30 g. active manganese dioxide is stirred for 5 hours at ambient temperature. The manganese dioxide is then filtered off with suction and the filtrate is evaporated. Yield 10.3 g. (94% of theory); m.p. 127°–128° C.

Another oxidation method is used for the preparation of 4-chlorobenzenesulphonic acid-[4-(3-oxopropyl)-phenethylamide].

Into a solution of 12.8 g. (59.4 mmole) pyridinium chlorochromate and 250 ml. methylene chloride are introduced, with stirring at ambient temperature, 14.0 g. (39.6 mmole) 4-chlorobenzenesulphonic acid-[4-(3-hydroxypropyl)-phenethylamide]. The reaction mixture is stirred for a further hour and then poured off from insolubles. The methylene chloride phase is chromatographed with a short column (silica gel/methylene chloride) and evaporated. Yield 10.8 g. (78% of theory); m.p. 65°–66° C. Oxime: m.p. 156°–158° C. (recrystallised from toluene).

EXAMPLE 6

4-Chlorobenzenesulphonic acid-[4-(3-oxobut-1-enyl)-phenethylamide]

A mixture of 3.2 g. (10 mnole) 4-chlorobenzenesulphonic acid-(4-formylphenethylamide), 50 ml. anhydrous toluene and 3.2 g. (10 mmole) 1-triphenylphosphoranylidene-2-propanone is refluxed for 5 hours, then cooled, stirred with silica gel and filtered off with suction. The filtrate is evaporated and purified by column chromatography (silica gel/methylene chloride). Yield 1.3 g. (36% of theory); m.p. 111°–113° C.

EXAMPLE 7

3-Trifluoromethylbenzenesulphonic acid-[4-(2-hydroxyethyl)-phenethylamide]

(a) By the reaction of 3-trifluoromethylbenzenesulphochloride with 4-(2-aminoethyl)-phenylacetic acid ethyl ester analogously to Example 1 there is obtained, in a yield of 76% of theory, ethyl 4-[2-(3-trifluoromethylbenezenesulphonylamino)-ethyl]-phenylacetate; m.p. 95°–97° C. (recrystallised from ethyl acetate). The acid prepared therefrom by hydrolysis melts at 119°–120° C. (recrystallised from toluene).

(b) Into a suspension of 0.92 g. (24 mmole) lithium aluminium hydride and 300 mI. anhydrous diethyl ether is dropped at ambient temperature a solution of 10.0 g. (24 mmole) ethyl 4-[2-(3-trifluoromethylbenzenesulphonyloamino)-ethyl]-phenylacetate in 200 ml. diethyl ether and the reaction mixture subsequently refluxed for 3 hours. After the decomposition of the reaction mixture with ice cold dilute acetic acid, the ether phase is separated off, the aqueous phase is shaken out with diethyl ether and the ether phases are combined, dried with anhydrous sodium sulphate and evaporated. The solid residue is recrystallised from toluene. Yield 7.6 g. (85% of theory) of the title compound; m.p. 70°–72° C.

When appropriate ethyl benzoates are reduced in an analogous way, the following compounds are obtained:

(2) 4-chlorobenzenesulphonic acid-(4-hydroxymethyl-phenethylamide); yield 85% of theory; m.p. 142°–143° C. (recrystallised from toluene+ethanol)

(3) 4-chlorobenzenesulphonic acid-[4-(5-hydroxypentyl)-phenethylamide]; yield 39% of theory: m.p. 80°–82° C. from ethyl 5-{4-[2-(4-chlorobenzenesulphonylamino)-ethyl]-phenyl}-pentanoate which is prepared analogously to Example 1 from 4-chlorobenzenesulphochloride and ethyl 5-[4-(2-aminoethyl)-phenyl]-pentanoate. Yield 89% of theory, colourless oil.

(4) 4-chlorobenzenesulphonic acid-[4-(2-hydroxyethyl)-benzylamide]; yield 61% of theory; m.p. 125°–127° C. (recrystallised from toluene+ethanol); from ethyl 4-(4-chlorobenzenesulphonylaminomethyl)-phenylacetate, which is prepared analogously to Example 1 from 4-chlorobenzenesulphochloride and ethyl 4-aminoethylphenylacetate; yield 81% of theory; m.p. 95°–96° C. (recrystallised from toluene).

(5) benzenesulphonic acid-[4-(2-hydroxyethyl)-phenethylamide]; yield 95% of theory; m.p. 70°–72° C.; from ethyl 4-[2-(benzenesulphonylamino)-ethyl]-phenylacetate, which is prepared analogously to Example 1 from benzenesulphochloride and ethyl 4-(2-aminoethyl)-phenylacetate; yield 87% of theory; colourless oil.

(6) 4-chlorobenzenesulphonic acid-[4-(2-hydroxyethyl)-phenethylamide]; yield 78% of theory: m.p. 84°–86° C. (recrystallised from toluene); from ethyl 4-[2-(4-chlorobenzenesulphonylanino)-ethyl]-phenylacetate, which is prepared analogously to Example 1 from 4-chlorobenzenesulphochloride and ethyl 4-(2-aminoethyl)-phenylacetate; yield 84% of theory; m.p. 93°–95° C. (recrystallised from heptane+toluene).

(7) 4-fluorobenzenesulphonic acid-[4-(2-hydroxyethyl)-phenethylamide]; yield 81% of theory; m.p. 78°–80° C. (recrystallised from toluene); from ethyl 4-[2-(4-fluorobenzenesulphonylamino)-ethyl]-phenylacetate, which is prepared analogously to Example 1 from 4-fluorobenzenesulphochloride and ethyl 4-(2-aminoethyl)phenylacetate; yield 87% of theory; m.p. 79°–81° C. (recrystallised from ethyl acetate).

(8) 4-methoxybenzenesulphonic acid-[4-(2-hydroxyethyl)-phenethylamide]; yield 58% of theory; m.p. 87°–89° C. (recrystallised from toluene); from ethyl 4-[2-(4-methoxybenzenesulphonylamino)-ethyl]-phenylacetate, which is prepared analogously to Example 1 from 4-methoxybenzenesulphochloride and ethyl 4-(2-aminoethyl)phenylacetate; yield 87% of theory; m.p. 85°–87° C.

(9) 4-isopropylbenzenesulphonic acid-[4-(2-hydroxyethyl)-phenethylamide]; yield 92% of theory; m.p. 81°–82° C. (recrystallised from toluene); from ethyl 4-[2-(4-isopropylbenzenesulphonylamino)-ethyl]-phenylacetate, which is prepared analogously to Example 1 from 4-isopropylbenzenesulphochloride and ethyl 4-(2-aminoethyl)phenylacetate; yield 72% of theory; m.p. 65°–67° C. (recrystallised from isopropanol).

In an analogous way, from the appropriate 3-phenylpropionic acid esters, there can be prepared the following compounds:

(10) 4-chlorobenzenesulphonic acid-[4-(5-hydroxypentyl)-phenethylamide]; yield 92% of theory; m.p. 80°–82° C.; from ethyl 5-{4-[2-(4-chlorobenzenesulphonylamino)-ethyl]-phenyl}-pentanoate, which is prepared analogously to Example 1 from 4-chlorobenzenesulphonylchloride and ethyl 5-[4-(2-aminoethyl)-phenyl]-pentanoate; yield 89% of theory; colourless oil.

(11) 4-chlorobenzenesulphonic acid-[4-(3-hydroxypropyl)-benzylamide]; yield 74% of theory; m.p. 92°–94° C. (recrystallised from toluene); from ethyl 3-[4-(4-chlorobenzenesulphonylamionmethyl)-phenyl]-propionate, which is prepared analogously to Example 1 from 4-chlorobenzenesulphonyl chloride and ethyl 3-4-(aminomethyl)-phenyl]-propionate;

yield 71% of theory; m.p. 93°–94° C. (recrystallised from toluene).

(12) 4-fluorobenzenesulphonic acid-[4-(3-hydroxypropyl)-phenethylamide]; yield 90% of theory; m.p. 77°–79° C. (recrystallised from toluene); from ethyl 3-{4-[2-(4-fluorobenzenesulphonylamino)-ethyl]-phenyl}-propionate, which is prepared analogously to Example 1 from 4-fluorobenzenesulphochloride and ethyl 3-[4-(2-aminoethyl)-phenyl]-propionate; yield 85% of theory; m.p. 52°–54° C. (recrystallised from cyclohexane+toluene).

(13) 4-chlorobenzenesulphonic acid-[4-(3-hydroxypropyl)-phenethylamide]; yield 75% of theory; m.p. 85°–86° C. (recrystallised from heptane+butyl acetate); from ethyl 3-{4-[2-(4-chlorobenzenesulphonylamino)-ethyl]-phenyl}-propionate; m.p. 65° C. (recrystallised from heptane+toluene)

(14) 3-chlorobenzenesulphonic acid-[4-(3-hydroxypropyl)-phenethylamide]; yield 74% of theory; m.p. 84°–86° C. (recrystallised from heptane+toluene); from ethyl 3-{4-[2-(3-chlorobenzenesulphonylamino)-ethyl]-phenyl}-propionate, which is prepared analogously to Example 1 from 3-chlorobenzenesulphochloride and ethyl 3-[4-(2-aminoethyl)-phenyl]-propionate; yield 94% of theory; m.p. 55°–57° C.

(15) 3-trifluoromethylbenzenesulphonic acid-[4-(3-hydroxypropyl)-phenethylamide]; yield 74% of theory; m.p. 64°–65° C. (recrystallised from ligroin+toluene), from ethyl 3-{4-[2-(3-trifluoromethylbenzenesulphonylamino)-ethyl]-phenyl}-propionate; m.p. 40°–41° C. (recrystallised from ligroin).

(16) methanesulphonic acid-[4-(3-hydroxypropyl)-phenethylamide]; yield 67% of theory; m.p. 81°–82° C. (recrystallised from water), from ethyl 3-{4-[2-(methanesulphonylamino)-ethyl]-phenyl}-propionate, which is prepared analogously to Example 1 from methanesulphochloride and ethyl 3-[4-(2-aminoethyl)-phenyl]-propionate; yield 78% of theory; m.p. 55°–56° C. (recrystallised from diethyl ether).

(17) n-hexanesulphonic acid-[4-(3-hydroxypropyl)-phenethylamide]; yield 69% of theory; m.p. 83°–84° C. (recrystallised from water), from ethyl 3-{4-[2-(n-hexanesulphoneslphonylamino)-ethyl]-phenyl}-propionate, which is prepared analogously to Example 1 from n-hexanesulphonyl chloride and ethyl 3-[4-(2-aminoethyl)-phenyl]-propionate; yield 84% of theory; m.p. 60°–61° C. (recrystallised from water).

(18) cyclohexanesulphonic acid-[4-(3-hydroxypropyl)-phenethylamide]; yield 87% of theory; m.p. 85°–86° C. (recrystallised from toluene); from ethyl 3-{4-[2-(cyclohexanesulphonylamino)-ethyl]-phenyl}-propionate, which is prepared analogously to Example 1 from cyclohexanesulphonyl chloride and ethyl 3-[4-(2-aminoethyl)-phenyl]-propionate; yield 73% of theory; colourless oil.

From the appropriate ethyl 4-phenylbutyrates, the following (4-hydroxybutyl)-phenyl compounds are prepared analogously:

(19) 4-fluorobenzenesulphonic acid-[4-(4-hydroxybutyl)-phenethylamide]; yield 75% of theory; m.p. 82°–84° C. (recrystallised from toluene), from ethyl 4-{4-[2-(2-fluorobenzenesulphoylamino)-ethyl]-phenyl}-butyrate, which is prepared analogously to Example 1 from 4-fluorobenzenesulphochloride and ethyl 4-[4-(2-aminoethyl)-phenyl]-butyrate; yield 92% of theory; colourless oil.

(20) 3-chlorobenzenesulphonic acid-[4-(4-hydroxybutyl)-phenethylamide]; yield 84% of theory; m.p. 85°–86° C. (recrystallised from heptane+toluene), from ethyl 4-{4-[2-(3-chlorobenzenesulphonylamino)-ethyl]-phenyl}-butyrate, which is prepared analogously to Example 1 from 3-chlorobenzenesulphochloride and ethyl 4-[4-(2-aminoethyl)-phenyl]-butyrate; yield 92% of theory; m.p. 34°–36° C. (wax-like).

(21) 4-chlorobenzenesulphonic acid-[4-(4-hydroxybutyl)-phenethylamide]; yield 87% of theory; m.p. 83°–85° C. (recrystallised from heptane+toluene), from ethyl 4-{4-[2-(4-chlorobenzenesulphonylamino)-ethyl]-phenyl}-butyrate, which is prepared analogously to Example 1 from 4-chlorobenzenesulphochloride and ethyl 4-[4-(2-aminoethyl)-phenyl]-butyrate; yield 91% of theory; m.p. 55°–58° C.

(22) 3,4-dichlorobenzenesulphonic acid-[4-(4-hydroxybutyl)-phenethylamide]; yield 71% of theory; m.p. 95°–97° C. (recrystallised from heptane+toluene), from ethyl 4-{4-[2-(3,4-dichlorobenzenesulphonylamino)-ethyl]-phenyl}-butyrate, which is prepared analogously to Example 1 from 3,4-dichlorobenzenesulphochloride and ethyl 4-[4-(2-aminoethyl)-phenyl]-butyrate; yield 86% of theory; m.p. 70°–73° C.

(23) 4-bromobenzenesulphonic acid-[4-(4-hydroxybutyl)-phenethylamide]; yield 89% of theory; m.p. 84°–85° C. (recrystallised from heptane+toluene), from ethyl 4-{4-[2-(4-bromobenzenesulphonylamino)-ethyl]-phenyl}-butyrate, which is prepared analogously to Example 1 from 4-bromobenzenesulphochloride and ethyl 4-[4-(2-aminoethyl)-phenyl]-butyrate; yield 90% of theory; m.p. 63°–64° C.

(24) 4-hydroxybenzenesulphonic acid-[4-(4-hydroxybutyl)-phenethylamide]; yield 63% of theory: m.p. 111°–112° C. (recrystallised from toluene), from ethyl 4-{4-[2-(4-hydroxybenzenesulphonylamino)-ethyl]-phenyl}-butyrate, which is prepared analogously to Example 1 from 4-hydroxybenzenesulphochloride and ethyl 4-[4-(2-aminoethyl)-phenyl]-butyrate; yield 86% of theory; colourless oil.

(25) 4-chlorobenzenesulphonic acid-{3-[4-(4-hydroxybutyl)-phenyl]-propylamide}; yield 81% of theory; m.p. 95°–97° C. (recrystallised from toluene), from ethyl 4-{4-[3-(4-chlorobenzenesulphonylamino)-propyl]-phenyl}-butyrate, which is prepared analogously to Example 1 from 4-chlorobenzenesulphochloride and ethyl 4-[4-(3-aminopropyl)-phenyl]-butyrate; yield 92% of theory: m.p. 71°–73° C. (recrystallised from heptane+toluene).

(26) 3-trifluoromethylbenzenesulphonic acid-[4-(4-hydroxybutyl)-phenethylamide]; yield 97% of theory; m.p. 72°–73° C. (recrystallised from ligroin+toluene), from ethyl 4-{4-[2-(3-trifluoromethylbenzenesulphonylamino)-ethyl]-phenyl}-butyrate, which is prepared analogously to Example 1 from 3-trifluoromethylbenzenesulphochloride and ethyl 4-[4-(2-aminoethyl)-phenyl]-butyrate; yield 92% of theory; colourless oil.

(27) 3-methoxybenzenesulphonic acid-[4-(4-hydroxybutyl)-phenethylamide]; yield 77% of theory, colourless oil; $n_D{}^{20}=1.5591$, from ethyl 4-{4-[2-(3-methoxybenzenesulphonylamino)-ethyl]-phenyl}-butyrate, which is prepared analogously to Example 1 from 3-methoxybenzenesulphochloride and ethyl 4-[4-(2-aminoethyl)-phenyl]-butyrate; yield 92% of theory; colourless oil.

(28) 3,4-dimethoxybenzenesulphonic acid-[4-(4-hydroxybutyl)-phenethylamide]; yield 79% of theory; m.p. 107°–109° C. (recrystallised from ethyl acetate), from ethyl 4-{4-[2-(3,4-dimethoxybenzenesulphonylamino)-ethyl]-phenyl}-butyrate, which is prepared analogously to Example 1 from 3,4-dimethoxybenzenesulphochloride and ethyl 4-[4-(2-aminoethyl)-phenyl]-butyrate; yield 72% of theory; colourless oil.

(29) 2-methylbenzenesulphonic acid-[4-(3-hydroxypropyl)-phenethylamide]; yield 82% of theory; colourless oil, from ethyl 3-{4-[2-(2-methylbenzenesulphonylamino)-ethyl]-phenyl}-propionate, which is prepared analogously to Example 1 from 2-methylbenzenesulphochloride and ethyl 3-[4-(2-aminoethyl)-phenyl]-propionate; yield 94% of theory: m.p. 50°–51° C. (recrystallised from cyclohexane).

(30) 1-naphthalenesulphonic acid-[4-(3-hydroxypropyl)-phenethylamide]; yield 78% of theory: m.p. 82°–83° C. (recrystallised from toluene); from ethyl 3-{4-[2-(1-naphthalenesulphonylamino)-ethyl]-phenyl-propionate, which is prepared analogously to Example 1 from 1-naphthalenesulphochloride and ethyl 3-[4-(2-aminoethyl)-phenyl]-propionate; yield 83% of theory: m.p. 73°–74° C.

(31) 4-chlorobenzenesulphonic acid-[4-(4-hydroxybutyl)-N-methylphenethylamide]; yield 53% of theory: colourless oil, from ethyl 4-{4-[2-(N-methyl-4-chlorobenzenesulphonylamino)-ethyl]-phenyl}-butyrate, which is prepared analogously to Example 1 from 4-chlorobenzenesulphochloride and ethyl 4-{4-[2-(methylamino)-ethyl]-phenyl}-butyrate; yield 72% of theory; colourless oil.

(32) 4-chlorobenzenesulphonic acid-[4-(4-hydroxybutyl)-N-benzylphenethylamide]; yield 68% of theory; m.p. 71°–72° C., from ethyl 4-{4-[2-(N-benzyl-4-chlorobenzenesulphonylamino)-ethyl]-phenyl}-butyrate, which is prepared analogously to Example 1 from 4-chlorobenzenesulphochloride and ethyl 4-{4-[2-(benzylamino)-ethyl]-phenyl}-butyrate; yield 82% of theory; m.p. 70°–71° C.

EXAMPLE 8

4-Azidobenzenesulphonic acid-[4-(2-hydroxyethyl)-phenethylamide]

To an ice cold solution of 5.5 g. (33 mmole) 4-(2-hydroxyethyl)-phenethylamine, 100 ml. methylene chloride and 3.4 g. (33 mmole) triethylamine is slowly added dropwise a solution of 7.2 g. (33 mmole) 4-azidobenzenesulphonyl chloride in 50 ml. methylene chloride. Subsequently, the reaction is allowed to continue for 1 hour with ice cooling. The reaction mixture is now shaken out twice with dilute sulphuric acid, then twice with water, dried with anhydrous sodium sulphate and finally evaporated. The residue is recrystallised twice from toluene to give 7.8 g. (64% of theory) of desired product; m.p. 90°–92° C. (recrystallised from toluene).

Analogously thereto, there are obtained:

(2) 4-cyanobenzenesulphonic acid-[4-(2-hydroxyethyl)-phenethylamide]; yield 51% of theory; m.p. 106°–108° C. (recrystallised from toluene), from 4-cyanobenzenesulphochloride and 4-(2-hydroxyethyl)-phenethylamine.

(3) 4-bromobenzenesulphonic acid-[4-(3-hydroxypropyl)phenethylamide]; yield 78% of theory: m.p. 82°–84° C. (recrystallised from heptane+toluene), from 4-bromobenzenesulphochloride and 4-(3-hydroxypropyl)-phenethylamine (4) 4-azidobenzenesulphonic acid-[4-(3-hydroxypropyl)-phenethylamide]; yield 39% of theory; m.p. 85°–88° C. (recrystallised from toluene), from 4-azidobenzenesulphochloride and 4-(3-hydroxypropyl)-phenethylamine (5) 4-nitrobenzenesulphonic acid-[4-(3-hydroxypropyl)-phenethylamide]; yield 69% of theory; m.p. 117°–118° C. (recrystallised from ethanol), from 4-nitrobenzenesulphochloride and 4-(3-hydroxypropyl)-phenethylamine (6) 4-cyanobenzenesulphonic acid-[4-(4-hydroxybutyl)-phenethylamide]; yield 55% of theory; m.p. 107°–109° C. (recrystallised from toluene), from 4-cyanobenzenesulphochloride and 4-(4-hydroxybutyl)-phenethylamine (7) 4-acetylbenzenesulphonic acid-[4-(4-hydroxybutyl)-phenethylamide]; yield 56% of theory; m.p. 109° C. (recrystallised from toluene), from 4-acetylbenzenesulphochloride and 4-(4-hydroxybutyl)-phenethylamine (8) 4-chlorostyrenesulphonic acid-[4-(3-hydroxypropyl)phenethylamide]; yield 62% of theory: m.p. 111°–112° C. (recrystallised from toluene), from 4-chlorostyrenesulphochloride and 4-(3-hydroxypropyl)-phenethylamine (9) 4-chlorobenzenesulphonic acid-[4-(1,3-dihydroxypropyl)-phenethylamide]; yield 23% of theory; m.p. 80°–82° C. (recrystallised from water), from 4-chlorobenzenesulphochloride and 4-(1,2-dihydroxypropyl)-phenethylamine.

EXAMPLE 9

4-Chlorophenylethanesulphonic acid-[4-(4-hydroxy-propyl)-phenethylamide]

(a) By the reaction of 4-chlorophenylethanesulphochloride with ethyl 3-[4-(2-aminoethyl)-phenyl]-propionate analogously to Example 1, there is obtained ethyl 3-{4-[2-(4-chlorophenylethanesulphonylamino)-ethyl]-phenyl}-propionate. Yield 80% of theory; m.p. 77°–78° C. (recrystallised from ethanol).

(b) To a boiling solution of 12.2 g. (28 mmole) of the ethyl ester obtained according to (a), 112 ml. tert.-butanol and 2.99 g. (79 mmole) sodium borohydride is added dropwise, within the course of 1 hour, 22.4 ml. methanol. The reaction mixture is maintained at reflux temperature for a further hour and then cooled. Water is added to the syrupy liquid, followed by evaporation in a vacuum and extraction with methylene chloride. The methylene chloride solution is dried with anhydrous sodium sulphate, then evaporated and the residue is recrystallised from toluene. Yield 9.08 g. (85% of theory) of title compound: m.p. 94°–95° C.

EXAMPLE 10

4-{4-[2-(3-Chlorobenzenesulphonylamino)-ethyl]-phenyl}-4-oxobutanoic acid (a) Ethyl 4-{4-[2-(acetamino)-ethyl]-phenyl}-oxobutanoate To a solution of 120.0 g. (0.74 mole) N-acetylphenethylamine and 1.4 liters 1,1,2,2-tetrachloroethane is added 146.0 g. (0.89 mole) succinic acid ethyl ester chloride. It is then cooled and 293 g. aluminium chloride are added portionwise thereto at 0° C. Stirring is continued for 1 hour at 0° C. and subsequently for 4 hours at ambient temperature, whereafter the reaction mixture is poured into an ice-hydrochloric acid mixture and the tetrachloroethane phase is separated off. It is washed with water and an aqueous solution of sodium carbonate, dried with anhydrous sodium sulphate and evaporated. The residue is recrystallised from ethyl acetate. Yield 157.4 g. (73% of theory); m.p. 111°–112° C.

(b) 4-[4-(2-Aminoethyl)-phenyl]-4-oxobutanoic acid

A mixture of 180.0 g. (0.62 mole) of the product obtained according to (a) and 1.3 l. 6N hydrochloric acid is kept at reflux temperature for 8 hours, then cooled in an ice bath and the precipitated crystals filtered off with suction. After washing with ice cold dilute hydrochloric acid and drying over potassium hydroxide, there are obtained 127.5 g. (76% of theory) of hydrochloride; m.p. 232°–234° C. (decomp.).

(c) Ethyl 4-[4-(2-aminoethyl)-phenyl-]4-oxobutanoate

On to a mixture of 127.2 g. (0.49 mole) of the acid obtained according to (b) and 800 ml. ethanol is passed, while stirring, gaseous hydrogen chloride and the reaction mixture is heated to reflux temperature for 2 hours, whereafter it is then strongly cooled. The precipitated crystals are filtered off with suction, washed with cold ethanol and dried over anhydrous calcium chloride. Yield 137.1 g. (97% of theory) of hydrochloride; m.p. 162°–165° C.

(d) Ethyl 4-{4-[2-(3-chlorobenzenesulphonylamino)-ethyl]-phenyl}-4-oxobutanoate

This is obtained by reacting the product obtained according to (c) with 3-chlorobenzenesulphochloride analogously to Example 1. Yield 81% of theory; m.p. 64°–66° C. (recrystallised from heptane+toluene).

(e) 4-{4-[2-(3-Chlorobenzenesulphonylamino)-ethyl]-phenyl}-4-oxobutanoic acid

A mixture of 5.0 g. (11.8 mmole) of the product obtained according to (d), 18 ml. 2N aqueous sodium hydroxide solution and 20 ml. methanol is stirred for 3 hours at 50° C. The methanol is then distilled off in a vacuum and the aqueous solution is extracted with diethyl ether. Subsequently, it is acidified with 6N hydrochloric acid and the precipitated acid is filtered off with suction, washed with water and dried over potassium hydroxide. Yield 4.6 g. (quantitative); m.p. 126°–128° C.

Analogously thereto, by reaction with the appropriate sulphonic acid chlorides and subsequent saponification, there are obtained the following compounds:

(2) ethyl 4-[4-(4-chlorobenzenesulphonylaminomethyl)-phenyl]-4-oxobutanoate; yield 97% of theory; m.p. 104°–106° C. (recrystallised from xylene); and therefrom 4-[4-(4-chlorobenzenesulphonylaminomethyl)-phenyl]-4-oxobutanoic acid; yield 76% of theory; m.p. 185°–186° C. (recrystallised from ethyl acetate)

(3) 4-{4-[2-(4-fluorobenzenesulphonylamino)-ethyl]-phenyl}-4-oxobutanoate; yield 76% of theory; m.p. 104°–105° C. (recrystallised from ethyl acetate); and therefrom 4-{4-[2-(4-fluorobenzenesulphonylamino)-ethyl]-phenyl}-4-oxobutanoic acid. yield 75% of theory; m.p. 138° C. (recrystallised from ethyl acetate)

(4) ethyl 4-{4-[2-(4-bromobenzenesulphonylamino)-ethyl]-phenyl}-4-oxobutanoate; yield 77% of theory; m.p. 108°–109° C. (recrystallised from toluene+heptane); and therefrom 4-{4-[2-(4-bromobenzenesulphonylamino)ethyl]-phenyl}-4-oxobutanoic acid; yield 96% of theory; m.p. 145°–148° C.

(5) ethyl 4-{4-[2-(3-trifluoromethylbenzenesulphonylamino)-ethyl]-phenyl-}-4-oxobutanoate: yield 86% of theory; m.p. 83°–85° C. (recrystallised from toluene); and therefrom 4-{4-[2-(3-trifluoromethylbenzenesulphonylamino)-ethyl]-phenyl}-4-oxobutanoic acid; yield 87% of theory; m.p. 120°–121° C. (recrystallised from toluene+ethyl acetate)

(6) ethyl 4-{4-[2-(2-methoxybenzenesulphonylamino)-ethyl]-phenyl}-4-oxobutanoate; yield 87% of theory; m.p. 82°–84° C. (recrystallised from toluene); and therefrom 4-{4-[2-(2-methoxybenzenesulphonylamino)-ethyl]-phenyl-}-4-oxobutanoic acid; yield 83% of theory; m.p. 146° C. (recrystallised from ethanol)

(7) ethyl 4-{4-[2-(4-chlorophenethylsulphonylamino)-ethyl]-phenyl}-4-oxobutanoate; yield 88% of theory; m.p. 112° C. (recrystallised from ethanol); and therefrom 4-{4-[2-(4-chlorophenethylsulphonylamino)-ethyl]-phenyl}-4-oxobutanoic acid: yield 74% of theory; m.p. 143°–144° C. (recrystallised from ethanol)

(8) ethyl 4-{4-[2-(4-chlorostyrenesulphonylamino)-ethyl]-phenyl}-4-oxobutanoate; yield 83% of theory; m.p. 98°–100° C. (recrystallised from ethanol); and therefrom 4-{4-[2-(4-chlorostyrenesulphonylamino)-ethyl]-phenyl}-4-oxobutanoic acid; yield 68% of theory; m.p. 152°–153° C. (recrystallised from toluene+ethyl acetate).

(9) ethyl 4-{4-[2-(4-hydroxybenzenesulphonylamino)-ethyl]-phenyl}-4-oxobutanoate; yield 64% of theory; m.p. 139°–142° C. (recrystallised from acetic acid); and therefrom 4-{4-[2-(4-hydroxybenzenesulphonylamino)-ethyl]-phenyl-}-4-oxobutanoic acid; yield 81% of theory; m.p. 163°–164° C. (recrystallised from ethanol)

(10) ethyl 4-{4-[2-(4-methoxybenzenesulphonylamino)-ethyl]-phenyl}-4-oxobutanoate; yield 85% of theory; m.p. 83°–84° C. (recrystallised from toluene)

(11) ethyl 4-{4-[2-(4-methylbenzenesulphonylamino)-ethyl]-phenyl-}-4-oxobutanoate; yield 71% of theory; m.p. 91°–92° C. (recrystallised from toluene).

With the use of ethyl 4-[4-(3-aminopropyl)-phenyl]-4-oxobutanoate, there is prepared:

(12) ethyl 4-4-[3-(4-chlorobenzenesulphonylamino)-propyl]-phenyl-4-oxobutanoate; yield 91% of theory; m.p. 84° C. (recrystallised from toluene); and therefrom 4-{4-[3-(4-chlorobenzenesulphonylamino)-propyl]-phenyl}-4-oxobutanoic acid; yield 95% of theory; m.p. 147°–149° C.

EXAMPLE 11.

4-{4-[2-(4-Chlorobenzenesulphonylamino)-ethyl]-phenyl}-4-oxobutanoic acid.

To a solution of 7.8 g. (30 mmole) 4-[4-(2-aminoethyl)-phenyl]-4-oxobutanoic acid hydrochloride, 45 ml. water and 8.4 g. (60 mmole) potassium carbonate is added portionwise at 80° C. 7.2 g. (34 mmole) 4-chlorobenzenesulphochloride. The reaction mixture is stirred for a further 1.5 hours at 80° C. and then cooled. It is then acidified and the precipitated acid is filtered off with suction, washed with water and dried. Yield 8.3 g. (69% of theory); m.p. 152° C. (recrystallised from aqueous acetone).

EXAMPLE 12.

Ethyl 4-{4-[2-(4-bromobenzenesulphonylamino)-ethyl]-phenyl}-4-hydroxybutanoate.

To a mixture of 8.0 g. (17.1 mmole) ethyl 4-{4-[2-(4-bromobenzenesulphonylamino)-ethyl]-phenyl}-4-oxobutanoate, 80 ml. ethanol and 30 ml. methanol is added portionwise, with stirring and ice cooling, 0.49 g. (12.8 mmole) sodium borohydride. Thereafter, the reaction mixture is stirred for 2 hours at ambient temperature, then evaporated in a vacuum. Methylene chloride and dilute hydrochloric acid are added thereto and shaken up and the phases are separated. The methylene chloride phase is washed with water, dried with anhydrous sodium sulphate and evaporated. After recrystallisation from ethanol, the yield is 5.4 g. (67% of theory) m.p. 99°–100° C.

In analogous way, the following esters are obtained:
(2) ethyl 4-[4-(4-chlorobenzenesulphonylaminomethyl)-phenyl]-4-hydroxybutanoate; yield 66% of theory; m.p. 93°–95° C. (recrystallised from ethanol)
(3) ethyl 4-{4-[2-(4-fluorobenzenesulphonylamino)-ethyl]-phenyl}-4-hydroxybutanoate; yield 71% of theory; m.p. 82°–83° C. (recrystallised from ethyl acetate+ligroin)
(4) ethyl 4-{4-[2-(3-chlorobenzenesulphonylamino)-ethyl]-phenyl}-4-hydroxybutanoate; yield 67% of theory; m.p. 78°–81° C. (recrystallised from ethanol)
(5) ethyl 4-{4-[2-(4-chlorobenzenesulohonylamino)-ethyl]-phenyl}-4-hydroxybutanoate; yield 92% of theory; colourless oil
(6) ethyl 4-{4-[2-(3-trifluoromethylbenzenesulphonylamino)-ethyl]-phenyl}-4-hydroxybutanoate; yield 81% of theory; colourless oil
(7) ethyl 4-{4-[2-(2-methoxybenzenesulphonylamino)-ethyl]-phenyl}-4-hydroxybutanoate; yield 74% of theory: colourless oil; $n_D^{20}$ 1.5417
(8) ethyl 4-{4-[2-(4-chlorophenethylsulphonylamino)-ethyl]-phenyl}-4-hydroxybutanoate; yield 97% of theory; colourless oil.

EXAMPLE 13.

Lactone of 4-{4-[2-(3-trifluoromethylbenzenesulphonylamino)-ethyl]-phenyl}-4-hydroxybutanoic acid.

To an ice cold solution of 9.0 g. (19.6 mmol) ethyl 4-{4-[2-(3-trifluoromethylbenzenesulphonylamino)-ethyl]-phenyl}-4-oxobutanoate and 150 ml. ethanol is added, in small portions, 1.0 g. (26.3 mmole) sodium borohydride, followed by stirring for 4 hours at ambient temperature. The ethanol is then distilled off in a vacuum and the residue is diluted with ice water and acidified with dilute sulphuric acid. An oil separates out which crystallises through. The crystals are filtered off with suction, dried and recrystallised from toluene. Yield 7.8 g. (86% of theory) of lactone; m.p. 98°–100° C.

EXAMPLE 14.

Lactone of 4-{4-[2-(4-bromobenzenesulphonylamino)-ethyl]-phenyl}-4-hydroxybutanoic acid.

This is obtained by heating a solution of 4.42 g. (10 mmole) 4-4-[2-(4-bromobenzenesulphonylamino)-ethyl]-phenyl}-4-hydroxybutanoic acid, 120 ml. toluene and a tip of p-toluenesulphonic acid for 4 hours. After cooling, the reaction mixture is shaken out with an aqueous solution of sodium bicarbonate, dried with anhydrous sodium sulphate and evaporated in a vacuum. Yield: quantitative; m.p. 95°–98° C.

In an analogous way, there is obtained:
(2) the lactone of 4-{4-[2-(3-chlorobenzenesulphonylamino)-ethyl]-phenyl}-4-hydroxybutanoic acid; yield quantitative; m.p. 78°–79° C.

EXAMPLE 15.

4-{4-[2-(4-Chlorobenzenesulphonylamino)-ethyl]-phenyl}-4-hydroxybutanoic acid.

A mixture of 11.0 g. (25.8 mmole) of the ethyl ester of the above acid, 30 ml. ethanol and 50 ml. 2N aqueous sodium hydroxide solution is refluxed for 5 hours, whereafter the ethanol is distilled off and the residue is diluted with water. The aqueous phase is extracted with ethyl acetate, then acidified with 2N sulphuric acid and again extracted with ethyl acetate. The organic phase is dried with anhydrous sodium sulphate and then evaporated. Yield 7.1 g. (69% of theory); m.p. 94°–95° C. (recrystallised from ethyl acetate +ligroin).

In analogous way are prepared:
(2) 4-4-2-(4-fluorobenzenesulphonylamino)-ethyl-phenyl)-4-hydroxybutanoic acid; yield 93% of theory; m.p. 94°–95° C.
(3) 4-4-2-(benzenesulphonylamino)-ethyl-phenyl-4-oxobutanoic acid; yield 97% of theory; m.p. 155°–156° C. (recrystallised from toluene +ethyl acetate)
(4) 4-4-2-(naphthalene-1-sulphonylamino)-ethyl-phenyl)-4-oxobutanoic acid; yield 85% of theory; m.p. 158°–156° C. (recrystallised from ethanol)
(5) 4-(4-[2-(N-methyl-4-chlorobenzenesulphonylamino)-ethyl]-phenyl)-4-oxobutanoic acid; yield 76% of theory; m.p. 118°–119° C. (recrystallised from ethanol)
(6) 4-4-2-(N-benzyl-4-chlorobenzenesulphonylamino)-ethyl]-phenyl)-4-oxobutanoic acid; yield 84% of theory; 157°–158° C. (recrystallised from ethanol +ethyl acetate)
(7) 4-{4-[2-[N-(4-chlorocinnamyl)-4-chlorobenzenesulphonylamino]-ethyl]-phenyl}-4-oxobutanoic acid; yield 80% of theory; m.p. 125°–126° C. (recrystallised from ethanol)
(8) 5-{4-2-(4-chlorobenzenesulphonylamino)-ethyl]-phenyl}-5-hydroxypentanoic acid; yield 91% of theory; m.p. 142°–143° C. (recrystallised from ethyl acetate)
(9) 5-{4-2-(4-chlorobenzenesulphonylamino)-ethyl-phenyl}-5-oxopentanoic acid; yield 88% of theory; m.p. 175°–176° C. (recrystallised from ethanol)
(10) 4-{4-2-4-(4-chlorophenyl)-benzenesulphonylamino]-ethyl]-phenyl}-4-oxobutanoic acid; yield 88% of theory; m.p. 191° C. (recrystallised from glacial acetic acid)

EXAMPLE 16.

4-{4-[2-(4-Bromobenzenesulphonylamino)-ethyl]-phenyl}-4-hydroxybutanoic acid.

The lactone of this hydroxy acid is dissolved in the calculated amount of warm 2N aqueous sodium hydroxide solution and cooled. An amount of acetic acid equivalent to the sodium hydroxide solution is now added, whereby the acid precipitates out. After washing with water and drying at ambient temperature over potassium hydroxide, the acid is obtained in practically quantitative yield (confirmed by MS and TLC) which, in the case of the melting point determination, immediately lactonises again.

EXAMPLES 17.

Disodium salt of 4-4-2-(3-chlorobenzenesulphonylamino)-ethyl]-phenyl}-4-hydroxybutanoic acid.

A mixture of the lactone of the above hydroxybutanoic acid is warmed with exactly two equivalents of aqueous sodium hydroxide solution (in the form of a 0.1 N aqueous solution), evaporated in a vacuum and dried in a vacuum desiccator over potassium hydroxide. Yield: quantitative m.p. from 145° C.

EXAMPLE 18.

4-Hydroxybenzenesulphonic acid-[4-(1,4-dihydroxybutyl)-phenethylamide].

To a suspension of 1.1 g. (29 mmole) lithium aluminium hydride and 50 ml. anhydrous tetrahydrofuran is added dropwise at ambient temperature a solution of 5.9 g. (14.5 mmole) ethyl 4-{4-[2-(4-hydroxybenzenesulphonyamino)-ethyl]-phenyl}-4-oxobutanoate in 100 ml. anhydrous tetrahydrofuran and the reaction mixture is subsequently refluxed for 6 hours. It is then decomposed with aqueous acetic acid, filtered off with suction from the hydroxide precipitate and the filtrate evaporated. The residue is taken up in ethyl acetate, dried with anhydrous sodium sulphate, evaporated and the residue recrystallised from ethyl acetate. Yield 2.6 g. (61% of theory); m.p. 133°–135° C.

In analogous way, there are prepared:
(2) 4-chlorobenzenesulphonic acid-4-(1,4-dihydroxybutyl)-benzylamide]; yield 56% of theory; m.p. 142°–143° C. (recrystallised from ethanol)
(3) 4-fluorobenzenesulphonic acid-[4-(1,4-dihydroxybutyl)phenethylamide]; yield 62% of theory; m.p. 75° 77° C. (recrystallised from ligroin +diethyl ether)
(4) 3-chlorobenzenesulphonic acid-[4-(1,4-dihydroxybutyl)phenethylamide]; yield 71% of theory; m.p. 75°–76° C. (recrystallised from butyl acetate)
(5) 4 chlorobenzenesulphonic acid-[4-(1,4-dihydroxybutyl)-phenethylamide]; yield 55% of theory; m.p. 101° C.
(6) 2-methoxybenzenesulphonic acid-[4 (1,4-dihydroxybutyl)-phenethylamide]; yield 74% of theory; colourless oil; $n_D^{20} = 1\ 5571$
(7) 4-methylbenzenesulphonic acid-[4-(1,4-dihydroxybutyl)phenethylamide]; yield 79% of theory; m.p. 103°–105° C. (recrystallised from ethyl acetate)
8) 4-methoxybenzenesulphonic acid-[4-(1,4-dihydroxybutyl)-phenethylamide]; yield 65% of theory; m.p. 78°–80° C. (recrystallised from ethyl acetate)
(9) 4-chlorobenzenesulphonic acid-{3-4-(1,4-dihydroxybutyl)-phenyl]-propylamie}butyl)-phenylpropylanide}; yield 85% of theory; m.p. 110°–112° C. (recrystallised from heptane +toluene)
(10) 3-trifluoromethylbenzenesulphonic acid-[4-(1,4-dihydroxybutyl)-phenethylamide]; yield 96% of theory; colourless oil
(11) benzenesulphonic acid-[4-(1,4-dihydroxybutyl)-phenethylamide]; yield 71% of theory; m.p. 96° 97° C. (recrystallised from toluene)

EXAMPLE 19.

4-Bromobenzenesulphonic acid-[4-(1,4-dihydroxybutyl)-phenethylamide].

To a solution of ethyl 4.0 g. (8.5 mmole) 4-{4-[2-(4-bromobenzenesulphonylamino)-ethyl]-phenyl}-4-hydroxybutanoate and 40 ml. tert.-butanol is added 1.0 g. (25.5 mmole) sodium borohydride. The reaction mixture is now heated to reflux temperature and 6.8 ml. methanol are added dropwise thereto, within the course of 1 hour. After heating for a further hour, it is evaporated, acidified with 2N sulphuric acid and shaken out with methylene chloride. The methylene chloride phase is dried with anhydrous sodium sulphate, evaporated and recrystallised from butyl acetate. Yield 3.36 g. (82% of theory); m.p. 125°–127° C.

In analogous way, there are prepared:
(2) 4-chlorophenethylsulphonic acid-4-(1,4-dihydroxybutyl)-phenethylamide]; yield 76% of theory; m.p. 105°–106° C. (recrystallised from toluene) from ethyl 4-}4-[2-(4-chlorophenethylsulphonylamino)-ethyl-phenyl}-4-hydroxybutanoate
(3) 4-chlorobenzenesulphonic acid-4-(1,5-dihydroxypentyl)-phenethylamide]; yield 76% of theory; m.p. 107°–108° C., from ethyl 5-}4-[2-(4-chlorobenzenesulphonylamino)-ethyl]-phenyl}- 5-hydroxypentanoate.

EXAMPLE 20.

Benzenesulphonic acid-[4-(4-hydroxy,1-oxobutyl)-phenethylamide].

30 g. Manganese dioxide are slowly added, with stirring, to a solution of 6.0 g. (17.2 mmole) benzenesulphonic acid-4 (1,4-dihydroxybutyl)-idenethylamide in 100 ml. methylene chloride, then further stirred for about 15 minutes and filtered off with suction. After evaporation and recrystallisation of the residue, first from butyl acetate and thereafter from a tolueneethanol mixture, there are obtained 3.2 g. (54% of theory) of the desired product; m.p. 89°–90° C. Upon heating, a slight decomposition occurs.

EXAMPLE 21. 4-Chlorobenzenesulphonic acid-[4-(2-acetoxyethyl)-N-acetylphenethylamide].

A solution of 2.54 g. (32 mmole) acetyl chloride in 25 ml. methylene chloride is slowly added dropwise at 0° C. to a suspension of 5.5 g. (16 mmole) 4-chlorobenzenesulphonic acid-4-(2-hydroxyethyl)-phenethylamide, 100 ml methylene chloride and 3.6 g. (36 mmole) triethylamine and then stirred for 2 hours at ambient temperature. Subsequently, washing is carried out with aqueous sodium carbonate solution, dilute hydrochloric acid and several times with water, followed by drying with anhydrous sodium sulphate and evaporation. After chromatography on silica gel with methylene chloride, there are obtained 4.0 g. (56% of theory) of the desired product in the form of a colourless oil.

The following compound is prepared in an analogous manner:
benzenesulphonic acid-4-(1-benzoyloxypropyl)-N-benzoyl-phenethylamide]; yield 82% of theory; colourless oil, from benzenesulphonic acid-4-(1-hydroxypropyl)-phenethylamide ] and 2 mole benzoyl chloride.

EXAMPLE 22.

4-Chlorobenzenesulphonic acid-(4-propionyl-N-acetylphenethylamide).

A solution of 3.57 g. (45.5 mmole) acetyl chloride in 50 ml. methylene chloride is slowly added dropwise to an ice-cold mixture of 16.0 g. (45.5 mmole) 4-chlorobenzenesulphonic acid-(4-propionylphenethylamide), 5.1 ml. (50 mmole) triethylamine and 200 ml. methylene chloride. The reaction mixture is then stirred for 3 hours at ambient temperature, extracted with 2N hydrochloric acid and several times with water, dried with anhydrous sodium sulphate and evaporated. After chromatography with silica gel/toluene +ethyl acetate (12:1 v/v), there are obtained 10.2 g. (57% of theory) of the desired product; m.p. 91°–92° C. (after recrystallisation from heptane +toluene).

The following compounds are obtained in an analogous manner from ethyl 4-{4-[2-(4-chlorobenzenesulphonylamino)-ethyl]-phenyl}-4-oxobutanoate and
(2) acetyl chloride:
ethyl 4-{4-[2-(N-acetyl-4-chlorobenzenesulphonylamino)ethyl]-phenyl}-4-oxobutanoate; yield 64% of theory; m.p. 107°–108° C.
(3) octanoyl chloride:
ethyl 4-{4-[2-(N-octanoyl-4-chlorobenzenesulphonylamino)-ethyl ethyl-phenyl-4-oxobutanoate; yield 69% of theory; m.p. 85°–86° C. (recrystallised from ethanol) 4) palmitoyl chloride: ethyl 4-4-2-(N-palmitoyl-4-chlorobenzenesulphonylamino)-ethyl]-phenyl}-4-oxobutanoate; yield 65% of theory; m.p. 86°–87° C. (recrystallised from ethanol)
(5) 4-chlorobenzoyl chloride: ethyl 4-{4-[2- N-(4-chlorobenzoyl)-4-chlorobenzenesulphonylamino)-ethyl]-phenyl}-4-oxobutanoate; yield 67% of theory: m.p. 104°–105° C. (recrystallised from ethanol).

EXAMPLE 23.

4-Chlorobenzenesulphonic acid-4-(2-hydroxyethyl)-N-octanoylphenethylamide].

A solution of 2.63 g. (16 mmole) octanoyl chloride in 25 ml. methylene chloride is slowly added dropwise at 0° C. to a mixture of 5.5 g. (16 mmole) 4-chlorobenzenesulphonic acid-4-(2-hydroxyethyl)-phenethylamide], 1.8 g. (18 mmole) triethylamine and 100 ml. methylene chloride. The reaction mixture is then maintained for 1 hour at 0° C. and for a further 2 hours at ambient temperature. It is subsequently shaken out with dilute hydrochloric acid and water, dried with anhydrous sodium sulphate and evaporated. After chromatography with silica gel/methylene chloride, there are obtained 3.8 g. (51% of theory of the desired product: m.p. 55° C.

The following compound is obtained in an analogous manner:
(2) with 4-chlorobenzoyl chloride:
4-chlorobenzenesulphonic acid-4-(2-hydroxyethyl)-N-(4-chlorobenzoyl)-phenethylamide]; yield 59% of theory; m.p. 112° C.

EXAMPLE 24.

4-Chlorobenzenesulphonic acid-[4-(4-hydroxybutyl)-N-(4-chlorocinnamyl)-phenethyloamide]. (4-chlorocinnamyl)-phenethylamide].

(a) Ethyl 4-4-2-[N-(4-chlorocinnamyl)-4-chlorobenzenesulphonylamino]-ethyl]-phenyl}-butyrate.

A sodium methylate solution which contains 24.4 mg. atom of sodium is added to a solution of 10.0 g. (24.4 mmole) ethyl 4-4-2-(4-chlorobenzenesulphonylamino)-ethyl]-phenyl}-butyrate in 80 ml. ethanol and then completely evaporated. The residue is stirred with diethyl ether and filtered off with suction with the exclusion of moisture. The salt obtained is dissolved in 50 ml. anhydrous dimethylformamide, 4.62 g. (24.7 mmole) 4-chlorocinnamyl chloride are added thereto and the reaction mixture is then kept for 3 hours at 80° C. After cooling, it is stirred into water, shaken out with diethyl ether and the ether phase is dried with anhydrous sodium sulphate. After evaporation, there are obtained 11.9 g. (87% of theory) of the desired product; m.p. 65°–67° C.

(b) 4-{4-[2-[N-(4-Chlorocinnamyl)-4-chlorobenzene-sulphonylamino]-ethyl]-phenyl}-butyric acid.

This is obtained by saponifying the ester obtained according to (a) analogously to Example 15. Yield 78% of theory: m.p. 112°–113° C. (recrystallisation from ethanol).

(c) A solution of 0.92 g. (8.5 mmole) ethyl chloroformate in 15 ml. anhydrous tetrahydrofuran is added dropwise, within the course of 15 minutes at −5° C., to a mixture of 4.5 g. (8.5 mmole) of the acid obtained according to b), 0.86 g. (8.5 mmole) anhydrous triethylamine and 30 ml. anhydrous tetrahydrofuran. The reaction mixture is then stirred for 30 minutes at −5° C., the precipitated triethylammonium chloride is filtered off with suction and the filtrate is added dropwise, in the course of 30 minutes at 10°–15° C., to an aqueous suspension of 0.8 g. (21 mmole) sodium borohydride. After stirring for 2 hours at ambient temperature, the tetrahydrofuran is distilled off, the residue is dissolved in 2N aqueous sodium hydroxide solution and the sodium hydroxide phase is extracted several times with methylene chloride. The extract is dried with anhydrous magnesium sulphate and evaporated. Water chromatography on silica gel with methylene chloride, there are obtained 2.4 g. (55% of theory) of the desired product; m.p. 80° C.

In a similar manner, there is carried out the preparation of
(2) 4-chlorobenzenesulphonic acid-4-(2-hydroxyethyl)-N-methylphenethylamide]; yield 61% of theory; colourless oil; by reacting ethyl 2-4-2-(4-chlorobenzenesulphonylamino)-ethyl]-phenyl}-acetate with methyl iodide and reducing the resultant ethyl 2-4-2-(N-methyl-4-chlorobenzenesulphonylamino)-ethyl-phenyl}-acetate (yield 56% of theory; colourless oil) with lithium aluminium hydride.

EXAMPLE 25.

With the use of the method described in Example 24 for the alkylation of sulphonamides, from ethyl 4-{4-[2-(4-chlorobenzenesulphonylamino)-ethyl]-phenyl}-4- oxobutanoate there are synthesised the following compounds using:
(1) methyl iodide:
ethyl 4-4-2-(N-methyl-4-chlorobenzenesulphonylamino)-ethyl]-phenyl}-4-oxobutanoate; yield 92% of theory. colourless oil
(2) benzyl chloride:
ethyl 4-b 4-2-(N-benzyl-4-chlorobenzenesulphonylamino)-ethyl]-phenyl}-4-oxobutanoate; yield 85% of theory: m.p. 99°–100° C. (recrystallised from ethanol)
(3) 4-chlorocinnamyl chloride:
ethyl 4-{4-[2-[N-(4-chlorocinnamyl)-4-chlorobenzenesulphonylamino]-ethyl]-phenyl}-4-oxobutanoate; yield 74% of theory; m.p. 78°–80° C. (recrystallised from ethanol); and from 4-chlorobenzenesulphonic acid-[4-(2-hydroxyethyl)-phenethylamide] and 4-chlorocinnamyl chloride:
(4) 4-chlorobenzenesulphonic acid-[N-(4-chlorocinnamyl)-4-(2-hydroxyethyl)-phenethylamide; yield 71% of theory; m.p. 100°–101° C. (recrystallised from toluene).

TEST PROTOCOL

Method:
Male mice of about 25 g body weight are used. The test substance is suspended in a 1% methyl cellulose solution and is administered to the test animals by way of an esophagus sonde. The provocation test consists therein that a dosage (800–1000 ug/kg) of Thromboxane-mimetic (U 46619 of UpJohn) which is lethal for the control animals is quickly injected into the tail vein. The specific antagonistic effect is tested by having the animals pretreated with mg/kg and the injection of U 46619 taking place after 4 hours. The survival rate, e.g., 4/5 indicates that 4 out of 5 animals tested have survived:

| Compound of Example | Survival Rate |
| --- | --- |
| 2.16 | 5/5 |
| 7.6 | 5/5 |
| 7.25 | 4/5 |
| 7.32 | 5/5 |
| 8.2 | 5/5 |
| 8.6 | 5/5 |
| 10.12 | 4/5 |
| 10.4 | 5/5 |
| 11 | 5/5 |
| 14 | 4/5 |
| 15 | 5/5 |
| 15.7 | 5/5 |
| 16 | 4/5 |
| 18.5 | 5/5 |
| 19 | 5/5 |
| 19.3 | 5/5 |
| 21 | 5/5 |
| 22.3 | 5/5 |
| 23.2 | 4/5 |
| 24 | 5/5 |

It will be understood that the specification and examples are illustrative but not limitative of the present invention and that other embodiments within the spirit and scope of the invention will suggest themselves to those skilled in the art.

What is claimed is:
1. A sulphonylphenylalkylamine compound of the formula:

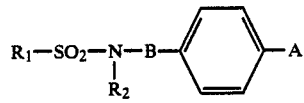

wherein
$R_1$ is $C_1$–$C_6$ alkyl, $C_3$–$C_7$ cycloalkyl, or an aralkyl, aralkenyl or aryl, the aryl moiety, in each case, having 6–14 carbon atoms and being unsubstituted or substituted at least once by halogen, $C_1$–$C_6$ alkyl, $C_1$–$C_6$ alkoxy, hydroxyl, trifluoromethyl, cyano, nitro, amino, $C_1$–$C_6$ alkylamino, $C_2$–$C_{12}$ dialkylamino, $C_1$–$C_6$ acylamino, $C_1$–$C_{16}$ acyl or azide;

$R_2$ is hydrogen, $C_1$–$C_6$ alkyl, $C_1$–$C_6$ acyl, or an aralkyl or aralkenyl, the aryl moiety, in each case, having 6–14 carbon atoms and being substituted at least once by halogen, $C_1$–$C_6$ alkyl, $C_1$–$C_6$ alkoxy, hydroxyl, trifluoromethyl, cyano, nitro, amino, $C_1$–$C_6$ alkylamino, $C_2$–$C_{12}$ dialkylamino, $C_1$–$C_6$ acylamino, $C_1$–$C_{16}$ acyl or azide;

B is an unbranched or branched $C_1$–$C_4$ alkylene chain and

A is $-COR_3$ OR $-CHOHR_3$ wherein $R_3$ is a $C_1$–$C_5$ alkyl, with a terminal hydroxyl or carboxyl group [$C_1$–$C_6$ alkyl, $C_2$–$C_6$ alkenyl, $Cl_1$–$C_6$ formylalkyl, $C_1$–$C_6$ hydroxyalkyl, a $C_1$–$C_6$ carboxyalkyl, a $C_1$–$C_6$ acetylalkenyl or a $-D-R_3$ group, in which D is a $-C-$ or $-CH-$ group and $R_3$ is a hydrogen, $C_1$–$C_5$ alkyl, $C_1$–$C_5$ hydroxylalkyl or a $C_1$–$C_5$-alkyl-carboxylic acid, or the pharmacologically acceptable salts thereof, the esters or amides thereof of those compounds which contain a hydroxyl and a carboxyl group.

2. The compound of claim 1, wherein
$R_1$ is methyl, ethyl, n-hexyl or cyclohexyl; phenethyl or styryl in which the phenyl moiety is unsubstituted or substituted by halogen; or phenyl which is unsubstituted by halogen; or phenyl which is unsubstituted or substituted by halogen, methyl, isopropyl, trifluoromethyl, methoxy, hydroxyl, cyano, nitro, azido, acetyl or acetylamino; or naphthyl or biphenyl unsubstituted or substituted by halogen;

$R_2$ is hydrogen, methyl, acetyl, octanoyl or hexadecanoyl or benzoyl unsubstituted or substituted by halogen; or benzyl, phenethyl or cinnamyl the phenyl moiety of which is unsubstituted or substituted by halogen;

B is methylene, ethylene or propylene; and A is $-COR_3$ or $-CHOHR_3$ wherein $R_3$ is a $C_1$–$C_5$ alkyl with a terminal hydroxyl or carboxyl group ethyl, propyl, butyl or pentyl which is unsubstituted or substituted once or twice with the same or a different group which can be hydroxyl, carboxyl, formyl, acetoxy or benzoyloxy; or hydroxymethyl, formyl, propenyl or acetylvinyl; or acetyl, propiopyl or butyryl which, in each case, can be substituted by hydroxyl, carboxyl, ethoxycarbonyl or methoxycarbonyl ; or pharmacologically acceptable salts thereof, esters or amides thereof, of those compounds which contain a hydroxyl and carboxyl group.

3. The compound of claim 1 designated 4-{4-[3-(4-chlorobenzenesulphonylamino)-propyl-]phenyl}-4-oxobutanoic acid.

4. The compound of claim 1 designated 4-bromobenzenesulphonic acid -[4- (1,4-dihydroxybutyl)-phenethylamide].

5. A pharmaceutical composition for the treatment of ailments due to increased thrombocyte aggregation or to a pathological change of kidney function comprising an effective amount of the compound of claim 1 to treat said ailment, in a physiologically acceptable carrier.

6. The pharmaceutical composition of claim 5 wherein said compound is
4-chlorobenzenesulphonic acid-4-(1,3-dihydroxypropyl)-phenethylamide];
4-chlorobenzenesulphonic acid-4-(1,4-dihydroxybutyl)-phenethylamide];
4-clorobenzenesulphonic acid-{3-4-(1,4-dihydroxybutyl)-phenyl]-propylamide};
benezenesulphonic acid-4-(1,4-dihydroxybutyl)-phenethylamide];
4-bromobenzenesulphonic acid-4-(1,4-dihydroxybutyl)-phenethylamide};
4-(-4-[3-(4-chlorobenzenesulphonylamino)-propyl-phenyl}-4-oxobutanoic acid;
4-(4-2-(4-bromobenzenesulphonylamino)-ethyl-phenyl)-4 hydroxybutanoic acid;
ethyl 4-[4-2-(N-octanoyl-4-chlorobenzenesulphonylamino) ethyl-phenyl)-4-oxobutanoate.

7. A method of treating increased thrombocyte aggregation or pathological change of kidney function comprising administering to the patient, an effective amount for treatment, of at least one of the compound of claim 1.

8. The method of claim 7 wherein 0.1 to 50 mg/kg body weight/day are administered.

9. The method of claim 8 wherein 0.5 to 40 mg/kg body weight/day are administered.

10. The method of claim 9 wherein 1.0 to 20 mg/kg bodyweight/day are administered.

11. A method for treating increased thrombocyte aggregation or pathological change of kidney function comprising administering to the patient, an effective amount for treatment, of at least one of the compound of claim 6.

12. A sulphonylphenylalkylamine compound of claim 1 consisting of 4-chlorobenzenesulphonic acid-4-(1,3-dihydroxypropyl)-phenethylamide.

13. A sulphonylphenylalkylamine compound of claim 1 consisting of 4-chlorobenzenesulphonic acid-4-(1,4-dihydroxybutyl)-phenylamide.

14. A sulphonylphenylalkylamine compound of claim 1 consisting of 4-clorobenzenesulphonic acid- 3-4-(1,4-dihydroxybutyl)-phenyl]-propylamide.

15. A sulphonylphenylalkylamine compound of claim 1 consisting of benezenesulphonic acid-4-(1,4-dihydroxybutyl)-phenethylamide.

16. The compound of claim 1 designated 4-{4-[2-(4-bromobenzenesulphonylamino)-ethyl]-phenyl}-4-hydroxybutanoic acid.

17. The compound of claim 1 designated ethyl-4-{4-(2-N(-octanoyl-4-chlorobenzene sulfonylamino)-ethyl]-phenyl}-4oxobutanoate.

* * * * *